(12) United States Patent
Curley

(10) Patent No.: US 11,950,829 B2
(45) Date of Patent: *Apr. 9, 2024

(54) METHODS AND DEVICES FOR USE OF DEGASSED FLUIDS WITH FLUID ENHANCED ABLATION DEVICES

(71) Applicant: Thermedical, Inc., Waltham, MA (US)

(72) Inventor: Michael G. Curley, Weston, MA (US)

(73) Assignee: Thermedical, Inc., Waltham, MA (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/465,780

(22) Filed: Sep. 2, 2021

(65) Prior Publication Data
US 2022/0047318 A1 Feb. 17, 2022

Related U.S. Application Data

(63) Continuation of application No. 16/373,104, filed on Apr. 2, 2019, now Pat. No. 11,135,000, which is a
(Continued)

(51) Int. Cl.
*A61B 18/04* (2006.01)
*A61B 18/08* (2006.01)
(Continued)

(52) U.S. Cl.
CPC ............ *A61B 18/082* (2013.01); *A61B 18/04* (2013.01); *A61B 18/1477* (2013.01);
(Continued)

(58) Field of Classification Search
CPC ... A61B 18/04; A61B 18/082; A61B 18/1477; A61B 18/16; A61B 2018/00029;
(Continued)

(56) References Cited

U.S. PATENT DOCUMENTS

| 4,160,455 A | 7/1979 | Law |
| 4,424,190 A | 1/1984 | Mather et al. |

(Continued)

FOREIGN PATENT DOCUMENTS

| CN | 1159154 A | 9/1997 |
| CN | 1323233 A | 11/2001 |

(Continued)

OTHER PUBLICATIONS

U.S. Appl. No. 13/445,034, filed Apr. 12, 2012, Devices and Methods for Remote Temperature Monitoring in Fluid Enhanced Ablation Therapy.

(Continued)

*Primary Examiner* — Michael F Peffley
(74) *Attorney, Agent, or Firm* — Barnes & Thornburg LLP

(57) ABSTRACT

Devices, systems, and methods for degassing fluid prior to applying fluid to a treatment site during ablation therapy are provided. In one embodiment, an ablation system can include an elongate body, an ablation element, a heating assembly, and a fluid source. Fluid in the fluid source can be at least partially degassed prior to being provided as part of the system, or, in some embodiments, a degassing apparatus can be provided that can be configured to degas fluid within the system prior to applying the fluid to the treatment site. The degassing apparatus can include one or more gas-permeable and fluid-impermeable tubes disposed therein, which can allow gas to be removed from fluid passing through the apparatus. Other exemplary devices, systems, and methods are also provided.

23 Claims, 6 Drawing Sheets

Related U.S. Application Data continuation of application No. 14/826,563, filed on Aug. 14, 2015, now Pat. No. 10,307,201, which is a continuation of application No. 14/536,212, filed on Nov. 7, 2014, now Pat. No. 9,138,288, which is a continuation of application No. 13/445,040, filed on Apr. 12, 2012, now Pat. No. 8,945,121.

(60) Provisional application No. 61/474,574, filed on Apr. 12, 2011.

(51) Int. Cl.
  A61B 18/14 (2006.01)
  A61B 18/16 (2006.01)
  F04B 17/03 (2006.01)
  F04B 41/02 (2006.01)
  A61B 17/00 (2006.01)
  A61B 18/00 (2006.01)
  F04B 19/22 (2006.01)
  F04B 43/04 (2006.01)
  F04B 49/06 (2006.01)

(52) U.S. Cl.
  CPC ............. *A61B 18/16* (2013.01); *F04B 17/03* (2013.01); *F04B 41/02* (2013.01); *A61B 2017/00526* (2013.01); *A61B 2018/00029* (2013.01); *A61B 2018/00041* (2013.01); *A61B 2018/00577* (2013.01); *A61B 2018/00642* (2013.01); *A61B 2018/00773* (2013.01); *A61B 2018/00791* (2013.01); *A61B 2018/00797* (2013.01); *A61B 2018/00809* (2013.01); *A61B 2018/00821* (2013.01); *A61B 2018/046* (2013.01); *A61B 2018/1425* (2013.01); *A61B 2018/162* (2013.01); *F04B 19/22* (2013.01); *F04B 43/04* (2013.01); *F04B 49/06* (2013.01); *F04C 2270/041* (2013.01); *Y10T 29/49016* (2015.01); *Y10T 29/49085* (2015.01)

(58) Field of Classification Search
  CPC ........... A61B 2018/00041; A61B 2018/00577; A61B 2018/00642; A61B 2018/00773; A61B 2018/00791; A61B 2018/00797; A61B 2018/00809; A61B 2018/00821; A61B 2018/046; A61B 2018/1425; A61B 2018/162; F04B 17/03; F04B 19/22; F04B 41/02; F04B 43/04; F04B 49/06; Y10T 29/49016; Y10T 29/49085; F04C 2270/041
  See application file for complete search history.

(56) References Cited

U.S. PATENT DOCUMENTS

| | | |
|---|---|---|
| 5,190,538 A | 3/1993 | Hussein et al. |
| 5,271,413 A | 12/1993 | Dalamagas et al. |
| 5,336,222 A | 8/1994 | Durgin et al. |
| 5,403,311 A | 4/1995 | Abele et al. |
| 5,409,487 A | 4/1995 | Jalbert et al. |
| 5,431,648 A * | 7/1995 | Lev ................ A61N 5/045 607/101 |
| 5,431,649 A | 7/1995 | Mulier et al. |
| 5,437,629 A | 8/1995 | Goldrath |
| 5,437,673 A | 8/1995 | Baust et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin et al. |
| 5,545,195 A | 8/1996 | Lennox et al. |
| 5,549,559 A | 8/1996 | Eshel |
| 5,573,510 A | 11/1996 | Isaacson |
| 5,609,151 A | 3/1997 | Mulier et al. |
| 5,653,692 A | 8/1997 | Masterson et al. |
| 5,697,949 A | 12/1997 | Giurtino et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,217,573 B1 | 4/2001 | Webster |
| 6,233,490 B1 | 5/2001 | Kasevich |
| 6,235,023 B1 | 5/2001 | Lee et al. |
| 6,238,393 B1 | 5/2001 | Mulier et al. |
| 6,272,370 B1 | 8/2001 | Gillies et al. |
| 6,302,904 B1 | 10/2001 | Wallstén et al. |
| 6,315,777 B1 | 11/2001 | Comben |
| 6,328,735 B1 * | 12/2001 | Curley ............... A61B 18/1492 606/14 |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,514,251 B1 | 2/2003 | Ni et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,025,768 B2 | 4/2006 | Elliott |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |

(56) References Cited

U.S. PATENT DOCUMENTS

| | | |
|---|---|---|
| 7,416,552 B2 | 8/2008 | Paul et al. |
| 7,468,057 B2 | 12/2008 | Ponzi |
| 7,507,222 B2 | 3/2009 | Cindrich et al. |
| 7,559,905 B2 | 7/2009 | Kagosaki et al. |
| 7,604,634 B2 | 10/2009 | Hooven |
| 7,666,166 B1 | 2/2010 | Emmert et al. |
| 7,815,590 B2 | 10/2010 | Cooper |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,061,120 B2 | 6/2015 | Osypka et al. |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |
| 9,877,768 B2 | 1/2018 | Curley et al. |
| 9,937,000 B2 | 4/2018 | Curley |
| 10,022,176 B2 | 7/2018 | Curley |
| 10,058,385 B2 | 8/2018 | Curley |
| 10,307,201 B2 | 6/2019 | Curley |
| 10,448,987 B2 | 10/2019 | Curley |
| 10,463,425 B2 | 11/2019 | Hoitink et al. |
| 10,548,654 B2 | 2/2020 | Curley |
| 10,881,443 B2 | 1/2021 | Curley |
| 11,013,555 B2 | 5/2021 | Curley et al. |
| 11,083,871 B2 | 8/2021 | Curley et al. |
| 11,135,000 B2 | 10/2021 | Curley |
| 11,583,330 B2 | 2/2023 | Curley |
| 2001/0031946 A1 | 10/2001 | Walker et al. |
| 2002/0026210 A1 | 2/2002 | Abdel-Gawwad |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0060862 A1 | 3/2003 | Goble et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0080410 A1 | 4/2005 | Rioux et al. |
| 2005/0090729 A1 | 4/2005 | Solis et al. |
| 2005/0165391 A1 | 7/2005 | Maguire et al. |
| 2005/0187543 A1 | 8/2005 | Underwood et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0241366 A1 | 10/2006 | Falwell et al. |
| 2006/0253183 A1 | 11/2006 | Thagalingam et al. |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0250053 A1 | 10/2007 | Fernald et al. |
| 2007/0250056 A1 | 10/2007 | Vanney |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161793 A1 | 7/2008 | Wang et al. |
| 2008/0161797 A1 | 7/2008 | Wang et al. |
| 2008/0167650 A1 | 7/2008 | Joshi et al. |
| 2008/0249463 A1 | 10/2008 | Pappone et al. |
| 2008/0275438 A1 | 11/2008 | Gadsby et al. |
| 2008/0275440 A1 | 11/2008 | Kratoska et al. |
| 2008/0281200 A1 | 11/2008 | Voic et al. |
| 2008/0288038 A1 | 11/2008 | Paul et al. |
| 2008/0294096 A1 | 11/2008 | Uber, III et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1* | 6/2009 | Sliwa ................. A61N 7/02 601/1 |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0048989 A1 | 2/2010 | Akahane |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2011/0282342 A1 | 11/2011 | Leo et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0253188 A1 | 10/2012 | Holland |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2013/0345670 A1 | 12/2013 | Rajagopalan et al. |
| 2014/0052117 A1 | 2/2014 | Curley |
| 2014/0058386 A1 | 2/2014 | Clark et al. |
| 2014/0155883 A1 | 6/2014 | Marion |
| 2014/0188106 A1 | 7/2014 | Curley |
| 2014/0275977 A1 | 9/2014 | Curley et al. |
| 2014/0276743 A1 | 9/2014 | Curley |
| 2014/0276758 A1 | 9/2014 | Lawrence et al. |
| 2014/0303619 A1 | 10/2014 | Pappone et al. |
| 2014/0350542 A1 | 11/2014 | Kramer et al. |
| 2015/0066025 A1 | 3/2015 | Curley |
| 2015/0223882 A1 | 8/2015 | Curley |
| 2015/0265344 A1 | 9/2015 | Aktas et al. |
| 2015/0297290 A1 | 10/2015 | Beeckler et al. |

(56) References Cited

U.S. PATENT DOCUMENTS

| | | |
|---|---|---|
| 2015/0351823 A1 | 12/2015 | Curley |
| 2015/0359582 A1 | 12/2015 | Curley et al. |
| 2016/0278856 A1 | 9/2016 | Panescu et al. |
| 2016/0354138 A1 | 12/2016 | Curley |
| 2017/0007324 A1 | 1/2017 | Kadamus et al. |
| 2017/0072193 A1 | 3/2017 | Heller et al. |
| 2017/0100582 A1 | 4/2017 | McEvoy et al. |
| 2017/0238993 A1 | 8/2017 | Curley |
| 2017/0296739 A1 | 10/2017 | Curley et al. |
| 2017/0333107 A1 | 11/2017 | Curley |
| 2018/0042669 A1 | 2/2018 | Curley et al. |
| 2018/0140345 A1 | 5/2018 | Curley et al. |
| 2018/0185083 A1 | 7/2018 | Curley |
| 2019/0290349 A1 | 9/2019 | Curley |
| 2019/0336729 A1 | 11/2019 | Curley et al. |
| 2020/0015880 A1 | 1/2020 | Curley |
| 2020/0113614 A1 | 4/2020 | Curley |
| 2020/0138502 A1 | 5/2020 | Curley |
| 2021/0393322 A1 | 12/2021 | Curley et al. |
| 2022/0032007 A1 | 2/2022 | Curley et al. |

FOREIGN PATENT DOCUMENTS

| | | |
|---|---|---|
| CN | 1341462 A | 3/2002 |
| CN | 1119127 C | 8/2003 |
| CN | 1456400 A | 11/2003 |
| CN | 1525839 A | 9/2004 |
| CN | 1211171 C | 7/2005 |
| CN | 1897885 A | 1/2007 |
| CN | 1942145 A | 4/2007 |
| CN | 2885157 Y | 4/2007 |
| CN | 101115527 A | 1/2008 |
| CN | 101209217 A | 7/2008 |
| CN | 101411645 A | 4/2009 |
| CN | 101578073 A | 11/2009 |
| CN | 101653375 A | 2/2010 |
| CN | 101773699 A | 7/2010 |
| CN | 201642316 U | 11/2010 |
| CN | 101999931 A | 4/2011 |
| CN | 101801445 B | 4/2013 |
| CN | 103930153 B | 9/2016 |
| CN | 103764056 B | 2/2017 |
| CN | 103619276 B | 7/2017 |
| CN | 103619275 B | 8/2017 |
| CN | 104869929 B | 11/2018 |
| CN | 105030325 B | 10/2019 |
| EP | 0 823 843 A1 | 2/1998 |
| EP | 895 756 A1 | 2/1999 |
| EP | 1 033 107 A1 | 9/2000 |
| EP | 1 159 036 A1 | 12/2001 |
| EP | 0 908 156 B1 | 11/2003 |
| EP | 2 042 112 A2 | 4/2009 |
| EP | 2 430 996 A2 | 3/2012 |
| EP | 1772109 B1 | 4/2015 |
| EP | 2207492 B1 | 3/2018 |
| JP | 62-211057 A | 9/1987 |
| JP | 01-146539 A | 6/1989 |
| JP | 05-212048 A | 8/1993 |
| JP | 10-505268 A | 5/1998 |
| JP | H11504539 A | 4/1999 |
| JP | 11-178787 A | 7/1999 |
| JP | 2001515368 A | 9/2001 |
| JP | 2001526098 A | 12/2001 |
| JP | 2003-528684 A | 9/2003 |
| JP | 2004024331 A | 1/2004 |
| JP | 2004275594 A | 10/2004 |
| JP | 2007509693 A | 4/2007 |
| JP | 2008080152 A | 4/2008 |
| JP | 2008-534081 A | 8/2008 |
| JP | 2009-504327 A | 2/2009 |
| JP | 2010505596 A | 2/2010 |
| JP | 2011-229920 A | 11/2011 |
| JP | 2014-516622 A | 7/2014 |
| JP | 2014516625 A | 7/2014 |
| JP | 2014518520 A | 7/2014 |
| JP | 2015205181 A | 11/2015 |
| JP | 2016209582 A | 12/2016 |
| JP | 6170037 B2 | 7/2017 |
| JP | 62-097971 | 3/2018 |
| JP | 6559186 B2 | 8/2019 |
| KR | 19990082587 A | 11/1999 |
| KR | 20140022887 A | 2/2014 |
| WO | 1994010948 A1 | 5/1994 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 1998033428 A2 | 8/1998 |
| WO | 99/20191 A1 | 4/1999 |
| WO | 99/32186 A1 | 7/1999 |
| WO | 02/089686 A1 | 11/2002 |
| WO | 03/028524 A3 | 10/2003 |
| WO | 03/096871 A2 | 11/2003 |
| WO | 2005/048858 A1 | 6/2005 |
| WO | 2005/089663 A1 | 9/2005 |
| WO | 2006/031541 A1 | 3/2006 |
| WO | 2006/055658 A1 | 5/2006 |
| WO | 2006/071058 A1 | 7/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2008083099 A1 | 7/2008 |
| WO | 2010/002733 A1 | 1/2010 |
| WO | 2010/151619 A2 | 12/2010 |
| WO | 2012/071058 A1 | 5/2012 |
| WO | 2018031281 A1 | 2/2018 |

OTHER PUBLICATIONS

U.S. Appl. No. 13/445,036, filed Apr. 12, 2012, Methods and Devices for Heating Fluid in Fluid Enhanced Ablation Therapy.

U.S. Appl. No. 13/445,040, filed Apr. 12, 2012, Mehtods and Devices for Use of Degassed Fluids With Fluid Enhanced Ablation Devices.

U.S. Appl. No. 13/445,365, filed Apr. 12, 2012, Devices and Methods for Dhaping Therapy in Fluid Enhanced Ablation.

U.S. Appl. No. 13/445,373, filed Apr. 12, 2012, Methods and Devices for Controlling Ablation Therapy.

U.S. Appl. No. 13/586,559, filed Aug. 15, 2012, Low Profile Fluid Enhanced Ablation Therapy Devices and Methods.

U.S. Appl. No. 13/837,295, filed Mar. 15, 2013, Methods and Devices for Fluid Enhanced Microwave Ablation Therapy.

U.S. Appl. No. 13/842,561, filed Mar. 15, 2013, Systems and Methods for Visualizing Fluid Enhanced Ablation Therapy.

U.S. Appl. No. 14/202,425, filed Mar. 10, 2014, Devices and Methods for Shaping Therapy in Fluid Enhanced Ablation.

U.S. Appl. No. 14/536,212, filed Nov. 7, 2014, Methods and Devices for Use of Degassed Fluids With Fluid Enhanced Ablation Devices.

U.S. Appl. No. 14/688,790, filed Apr. 16, 2015, Methods and Devices for Fluid Enhanced Microwave Ablation Therapy.

U.S. Appl. No. 14/826,549, filed Aug. 14, 2015, Methods and Devices for Heating Fluid in Fluid Enhanced Ablation Therapy.

U.S. Appl. No. 14/826,563, filed Aug. 14, 2015, Methods and Devices for Use of Degassed Fluids With Fluid Enhanced Ablation Devices.

U.S. Appl. No. 15/234,858, filed Aug. 11, 2016, Devices and Methods for Delivering Fluid to Tissue During Ablation Therapy.

U.S. Appl. No. 15/240,693, filed Aug. 18, 2016, Methods and Devices for Controlling Ablation Therapy.

U.S. Appl. No. 15/450,806, filed Mar. 6, 2017, Devices and Methods for Remote Temperature Monitoring in Fluid Enhanced Ablation Therapy.

U.S. Appl. No. 15/476,371, filed Mar. 31, 2017, Systems and Methods for Visualizing Fluid Enhanced Ablation Therapy.

U.S. Appl. No. 15/663,914, filed Jul. 31, 2017, Devices and Methods for Shaping Therapy in Fluid Enhanced Ablation.

(56) References Cited

OTHER PUBLICATIONS

U.S. Appl. No. 15/663,929, filed Jul. 31, 2017, Devices and Methods for Delivering Fluid to Tissue During Ablation Therapy.
U.S. Appl. No. 15/861,359, filed Jan. 3, 2018, Methods and Devices for Heating Fluid in Fluid Enhanced Ablation Therapy.
U.S. Appl. No. 15/909,103, filed Mar. 1, 2018, Methods and Devices for Controlling Ablation Therapy.
U.S. Appl. No. 15/970,543, filed May 3, 2018, Selectively Deployable Catheter Ablation Devices.
U.S. Appl. No. 16/035,797, filed Jul. 16, 2018, Inferred Maximum Temperature Monitoring for Irrigated Ablation Therapy.
U.S. Appl. No. 16/373,104, filed Apr. 2, 2019, Methods and Devices for Use of Degassed Fluids With Fluid Enhanced Ablation Devices.
U.S. Appl. No. 16/660,212, filed Oct. 22, 2019, Methods and Devices for Controlling Ablation Therapy.
U.S. Appl. No. 16/673,305, filed Nov. 4, 2019, Systems and Methods for Visualizing Fluid Enhanced Ablation Therapy.
U.S. Appl. No. 16/720,581, filed Dec. 19, 2019, Devices and Methods for Remote Temperature Monitoring in Fluid Enhanced Ablation Therapy.
U.S. Appl. No. 17/244,145, filed Apr. 29, 2021, Devices and Methods for Delivering Fluid to Tissue During Ablation Therapy.
U.S. Appl. No. 17/367,283, filed Jul. 2, 2021, Devices and Methods for Selectively Deploying Catheter Instruments.
**Kalman et al., "Biophysical characteristics of radiofrequency lesion formation in vivo: Dynamics of catheter tip-tissue contact evaluated by intracardiac echocardiography," American Heart Journal, vol. 133, Issue 1, 1997, pp. 8-18.
**Marrouche et al., "Phased-array intracardiac echocardiography monitoring during pulmonary vein isolation in patients with atrial fibrillation: impact on outcome and complications," Circulation. Jun. 3, 2003. 107(21):2710-6.
**Nath et al., Prog. Card. Dis. 37(4):185-204 (1995).
**Oh et al., "Avoiding microbubbles formation during radiofrequency left atrial ablation versus continuous microbubbles formation and standard radiofrequency ablation protocols: comparison of energy profiles and chronic lesion characteristics," J Cardiovasc Electrophysiol. Jan. 2006. 17(1):72-7.
**Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
**Saliba et al., "Intracardiac echocardiography during catheter ablation of atrial fibrillation, "Europace. 2008. 0:0-0.
**Sapareto et al., Int. J Rad. One. Biol. Phys. 10(6):787-800 (1984).
**Steinberg et al., "Intracranial Emboli Associated With Catheter Ablation of Atrial Fibrillation. Has the Silence Finally Been Broken?" JACC. 2011. 58(7):689-91.
**Takami et al., "Effect of Left Atrial Ablation Process and Strategy on Microemboli Formation During Irrigated Radiofrequency Catheter Ablation in an In Vivo Model," Circ Arrhythm Electrophysiol. 2016. 9:e003226.
**Young, S.T., et al., An instrument using variation of resistance to aid in needle tip insertion in epidural block in monkeys. Med Instrum. Oct. 1987;21(5):266-8. Abstract Only.
**Anselmino et al., "Silent Cerebral Embolism during Atrial Fibrillation Ablation: Pathophysiology, Prevention and Management," J Atr Fibrillation. Aug. 31, 2013. 6(2):796.
**Brace CL. Microwave tissue ablation: biophysics, technology, and applications. Crit Rev Biomed Eng. 2010;38(1):65-78.
**Calkins et al., Document Reviewers: 2017 "HRS/EHRA/ECAS/APHRS/SOLAECE expert consensus statement on catheter and surgical ablation of atrial fibrillation," Europace. Jan. 1, 2018. 20(1):e1-e160.
**Chinese Office Action for Application No. 201280028609.9, dated May 27, 2015. (22 bages).
**Chinese Office Action for Application No. 201280028611.6, dated Jul. 29, 2015. (23 pages).
**Chinese Office Action for Application No. 201280028612.0, dated Nov. 2, 2016. (8 pages).
**Chinese Office Action for Application No. 201280028620.5, dated May 27, 2015. (26 pages).
**Chinese Office Action for Application No. 201280028621.X, dated Jul. 31, 2015. (18 pages).
**Chinese Office Action for Application No. 201380053690.0, dated Jul. 20, 2017. (18 pages).
**Chinese Office Action for Application No. 201380053690.0, dated Sep. 30, 2016. (17 pages).
**Chinese Office Action for Application No. 2016112115279.0, dated Nov. 30, 2018. (15 pages).
**Chinese Office Action for Application No. 201611215279.0, dated Aug. 12, 2019. (21 pages).
*Chinese Office Action for Application No. 201710537279.0, issued Apr. 3, 2019. (Docket No. 111028-100) (8 pages).
**David R. Lide (ed)., CRC Handbook of Chemistry and Physics, 87th Edition. 2006. p. 8-81. CRC Press, Florida.
**Dello Russo et al., "Role of Intracardiac echocardiography in Atrial Fibrillation Ablation," J Atr Fibrillation. Apr. 6, 2013. 5(6):786.
**European Invitation to Attend Oral Proceedings for Application No. 12771601.7 dated Feb. 19, 2020 (7 Pages).
**European Office Action for Application No. 12771601.7, dated Jun. 13, 2018 (5 pages).
**European Office Action for Application No. EP 12771876.5, dated May 31, 2018 (6 pages).
**Extended European Search Report and Search Opinion for Application No. 13829821.1 dated Mar. 17, 2016 (7 pages).
**Extended European Search Report and Search Opinion for Application No. 19151775.4 issued May 21, 2019 (8 pages).
**Extended European Search Report and Written Opinion for Application No. 12771601.7 dated Oct. 27, 2014 (7 pages).
**Extended European Search Report for Application No. 20184347.1 dated Feb. 1, 2021 (8 pages).
**Extended Search Report and Written Opinion for EP 12770537.4 dated Oct. 10, 14 (6 pages).
**Extended Search Report and Written Opinion for EP 12770631.5 dated Oct. 1, 2014.
**Extended Search Report and Written Opinion for EP 12771331.1 dated Sep. 25, 2014.
**Extended Search Report and Written Opinion for EP 12771876.5 dated Oct. 13, 2014 (6 pages).
Extended European Search Report for Application No. 19796516.3 dated Dec. 2, 2021 (8 Pages).
**Goya et al., "The use of intracardiac echocardiography catheters in endocardial ablation of cardiac arrhythmia: Meta-analysis of efficiency, effectiveness, and safety outcomes," J Cardiovasc Electrophysiol. Mar. 2020. 31(3):664-673.
**Haines et al., "Microembolism and Catheter Ablation I A Comparison of Irrigated Radiofrequency and Multielectrode-phased Radiofrequency Catheter Ablation of Pulmonary Vein Ostia," Circ Arrhythm Electrophysiol. 2013. 6:16-22.
**Haines et al., "Microembolism and Catheter Ablation II Effects of Cerebral Microemboli Injection in a Canine Model," Circ Arrhythm Electrophysiol. 2012. 6:23-30.
**Haines, "Asymptomatic Cerebral Embolism and Atrial Fibrillation Ablation. What Price Victory?" Circ Arrhythm Electrophysiol. 2013. 6:455-457.
**Hijazi et al., "Intracardiac echocardiography during interventional and electrophysiological cardiac catheterization.," Circulation. Feb. 3, 2009. 119(4):587-96.
**International Invitation to Pay Additional Fees for Application No. PCT/US2017/044706, dated Oct. 5, 2017 (2 Pages).
**International Search Report and Written Opinion for Application No. PCT/US19/30645, dated Jul. 22, 2019 (14 pages).
**International Search Report and Written Opinion for Application No. PCT/US2012/033203, dated Sep. 21, 2012. (23 pages).
**International Search Report and Written Opinion for Application No. PCT/US2012/033213, dated Sep. 21, 2012. (17 pages).
**International Search Report and Written Opinion for Application No. PCT/US2012/033216, dated Sep. 21, 2012. (17 pages).
**International Search Report and Written Opinion for Application No. PCT/US2012/033327, issued Sep. 21, 2012. (14 pages).
**International Search Report and Written Opinion for Application No. PCT/US2012/033332, dated Sep. 21, 2012. (20 pages).

(56) References Cited

OTHER PUBLICATIONS

**International Search Report and Written Opinion for Application No. PCT/US2013/053977, dated Nov. 14, 2013. (20 pages).
**International Search Report and Written Opinion for Application No. PCT/US2014/024731, dated Jul. 21, 2014 (39 pages).
**International Search Report and Written Opinion for Application No. PCT/US2017/044706, dated Nov. 29, 2017 (25 pages).
**Japanese Office Action for Application No. 2014-505263, dated Jan. 26, 2016 (4 pages).
**Japanese Office Action for Application No. 2014-505266, dated Feb. 23, 2016 (7 pages).
**Japanese Office Action for Application No. 2017-151156, dated Apr. 16, 2019 (23 pages).
**Japanese Office Action for Application No. 2017-151156, dated Aug. 7, 2018 (11 bages).
**Japanese Office Action for Application No. 2017-207454, dated Oct. 2, 2018 (6 pages).
**Japanese Office Action for Application No. 2018-029767, dated Sep. 4, 2018 (5 bages).
Japanese Office Action for Application No. 2019-507789, dated Jun. 29, 2021 (13 pages).
**Jongbloed et al., "Clinical applications of intracardiac echocardiography in interventional procedures," Heart. Jul. 2005. 91(7):981-90.
Chinese Search Report for Application No. 201711019074, dated Nov. 26, 2019 (2 pages).
Chinese Supplementary Search for Application No. 201711019074, dated Feb. 29, 2020 (1 page).
Chinese First Search for Application No. 201780062751, dated Dec. 28, 2021 (1 page).
Chinese Office Action for Application No. 201980043984.2, dated May 31, 2022. (9 pages).
Chinese Office Action for Application No. 201780062751.8, dated Jul. 1, 2022. (19 pages).
Extended European Search Report for Application No. 19837499.3 dated Apr. 8, 2022 (11 pages).
European Office Action for U.S. Appl. No. 19/151,775, dated Feb. 2, 2023 (4 pages).
Japanese Office Action for Application No. 2019-507789, dated May 24, 2022 (11 pages).
Japanese Office Action for Application No. 2020-561818, dated Apr. 4, 2023.
Japanese Search Report for Application No. 2020-557181, dated Apr. 21, 2023 (19 pages).
Korean Office Action for Application No. 10-2019-7005130, dated Jan. 26, 2022 (12 pages).
Korean Office Action for Application No. 10-2021-7023589, dated Sep. 29, 2022 (10 pages).

* cited by examiner

METHODS AND DEVICES FOR USE OF DEGASSED FLUIDS WITH FLUID ENHANCED ABLATION DEVICES

RELATED APPLICATIONS

This application is a continuation of U.S. application Ser. No. 16/373,104, filed on Apr. 2, 2019, and now issued as U.S. Pat. No. 11,135,000. U.S. application Ser. No. 16/373,104 is a continuation of U.S. application Ser. No. 14/826,563, filed on Aug. 14, 2015, and now issued as U.S. Pat. No. 10,307,201. U.S. application Ser. No. 14/826,563 is a continuation of U.S. application Ser. No. 14/536,212, filed on Nov. 7, 2014 and now issued as U.S. Pat. No. 9,138,288. U.S. application Ser. No. 14/536,212 is a continuation of U.S. application Ser. No. 13/445,040, filed on Apr. 12, 2012 and now issued as U.S. Pat. No. 8,945,121. U.S. application Ser. No. 13/445,040 claims priority to U.S. Provisional Appl. No. 61/474,574, filed on Apr. 12, 2011, and entitled "Improvement in Ablation Catheters." This application is also related to U.S. application Ser. No. 13/445,034 entitled "Devices and Methods for Remote Temperature Monitoring in Fluid Enhanced Ablation Therapy," now abandoned, U.S. application Ser. No. 13/445,036 entitled "Methods and Devices for Heating Fluid in Fluid Enhanced Ablation Therapy," now issued as U.S. Pat. No. 9,138,287, U.S. application Ser. No. 13/445,373 "Methods and Devices for Controlling Ablation Therapy," now issued as U.S. Pat. No. 9,445,861, and U.S. application Ser. No. 13/445,365 "Devices and Methods for Shaping Therapy in Fluid Enhanced Ablation," now issued as U.S. Pat. No. 8,702,697, all of which were filed concurrently with U.S. application Ser. No. 13/445,040. The disclosures of each of these applications are hereby incorporated by reference in their entirety.

GOVERNMENT RIGHTS

This invention was made with government support under grants CA69926 and HL63535 awarded by The National Institutes of Health. The government has certain rights in the invention.

FIELD

The invention relates generally to fluid enhanced ablation, such as the SERFTM ablation technique (Saline Enhanced Radio FrequencyTM ablation), and more particularly relates to methods and devices for degassing fluid introduced into tissue during fluid enhanced ablation.

BACKGROUND

The use of thermal energy to destroy bodily tissue can be applied to a variety of therapeutic procedures, including the destruction of tumors. Thermal energy can be imparted to the tissue using various forms of energy, such as radio frequency electrical energy, microwave or light wave electromagnetic energy, or ultrasonic vibrational energy. Radio frequency (RF) ablation, for example, can be effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, maximum heating can occur in the tissue immediately adjacent to the emitting electrode. This can reduce the conductivity of the tissue, and in some cases, can cause water within the tissue to boil and become water vapor. As this process continues, the impedance of the tissue can increase and prevent current from entering into the surrounding tissue. Thus, conventional RF instruments are limited in the volume of tissue that can be treated.

Fluid enhanced ablation therapy, such as the SERFTM ablation technique (Saline Enhanced Radio FrequencyTM ablation), can treat a greater volume of tissue than conventional RF ablation. The SERF ablation technique is described in U.S. Pat. No. 6,328,735, which is hereby incorporated by reference in its entirety. Using the SERF ablation technique, saline is passed through a needle and heated, and the heated fluid is delivered to the tissue immediately surrounding the needle. The saline helps distribute the heat developed adjacent to the needle and thereby allows a greater volume of tissue to be treated with a therapeutic dose of ablative energy. The therapy is usually completed once a target volume of tissue reaches a desired therapeutic temperature, or otherwise receives a therapeutic dose of energy.

One problem that can arise in fluid enhanced ablation therapy is that gas dissolved in the fluid can come out of solution due to heating that occurs before or during its introduction into the volume of tissue to be treated. When gas comes out of solution, it introduces a compressible gas into a system otherwise filled with an incompressible fluid. The compliance of the compressible gas can introduce a number of complications into the fluid enhanced ablation system and, as the amount of compliance in the system increases, the efficiency and effectiveness of the treatment can decrease. For example, bubbles formed from gas coming out of solution in the fluid (e.g., as the result of localized super-heating of the fluid near an RF electrode) can affect the fluid flow rate since the gas bubbles are compressible and can absorb pressure created by a fluid pump. Variance in the fluid flow rate can, in turn, reduce the volume of tissue that can be treated and make ablation therapy less reliable and reproducible. Still further, introducing gas bubbles into tissue within the body can, in some circumstances, have unintended and undesirable medical consequences for a patient.

Accordingly, there remains a need for improved devices and methods for fluid enhanced ablation therapy.

SUMMARY

Devices, systems, and methods are generally provided for improving ablation therapy by degassing fluid provided in conjunction with such therapy. In one embodiment of an ablation system, the system can include an elongate body, an ablation element, a heating assembly, and a fluid source. The elongate body can have proximal and distal ends, an inner lumen extending through the elongate body, and at least one outlet port formed in the elongate body and configured to deliver fluid to tissue surrounding the elongate body. The ablation element can be disposed along a length of the elongate body adjacent to the at least one outlet port, and it can be configured to heat tissue surrounding the ablation element when the elongate body is inserted into tissue. The heating assembly can be disposed within the inner lumen, adjacent to the ablation element, and it can be configured to heat fluid flowing through the inner lumen. The fluid source can be in fluid communication with the inner lumen such that fluid can be delivered from the fluid source and through the inner lumen. The fluid source can contain a volume of fluid that is at least partially degassed such that the fluid contains one or more gases having a predetermined pressure and mixture.

A pump can be coupled to the fluid source and it can be configured to pump fluid from the fluid source and through the inner lumen of the elongate body. In some embodiments, a mass exchanger can be coupled to the fluid source and it can be configured to at least partially degas the fluid of the fluid source. The fluid source can include a syringe that is configured to couple to the elongate body for delivering fluid to the inner lumen. In some embodiments, the fluid can be saline. Further, a sensor can be included as part of the system. The sensor can be configured to measure an amount of gas in the fluid.

In another exemplary embodiment of an ablation system, the system can include an elongate body, an ablation element, a heating assembly, and a mass exchanger. The elongate body can have proximal and distal ends, an inner lumen extending through the elongate body, and at least one outlet port formed in the elongate body and configured to deliver fluid to tissue surrounding the elongate body. The ablation element can be disposed along a length of the elongate body adjacent to the at least one outlet port, and it can be configured to heat tissue surrounding the ablation element when the elongate body is inserted into tissue. The heating assembly can be disposed within the inner lumen, adjacent to the ablation element, and it can be configured to heat fluid flowing through the inner lumen. The mass exchanger can be in fluid communication with fluid flowing through the inner lumen, and further, it can be configured to at least partially degas fluid flowing through the inner lumen.

The mass exchanger can include a plurality of gas-permeable and fluid-impermeable tubes, as well as at least one outlet configured to couple to a gas source for adjusting the amount of gas in the fluid flowing through the plurality of gas-permeable and fluid-impermeable tubes. The gas source can include a vacuum source for removing gas from the fluid. Alternatively, the gas source can include one or more gases having a predetermined pressure and mixture. The mass exchanger can be disposed proximal of the heating assembly such that fluid is at least partially degassed before being heated by the heating assembly. In some embodiments, the mass exchanger can be disposed within a control unit coupled to a proximal end of the elongate body. The control unit can include a pump that is effective to pump fluid from a fluid source, through the mass exchanger, and into the inner lumen of the elongate body. The system can further include a sensor that can be configured to measure an amount of a gas in fluid after it flows through the mass exchanger.

Methods for ablating tissue are also provided, and in one exemplary embodiment, the method can include inserting an elongate body into a tissue mass, delivering fluid that is at least partially degassed through an inner lumen of the elongate body, delivering energy to at least one heating assembly disposed within the inner lumen to heat the at least partially degassed fluid within the lumen, and delivering energy to an ablation element. The at least partially degassed fluid can contain one or more gases having a predetermined pressure and mixture. The fluid can flow through at least one outlet port in the elongate body and into the tissue mass. Further, delivering energy to an ablation element can occur simultaneously with delivering energy to the at least one heating assembly, to ablate the tissue mass.

In some embodiments, prior to delivering the at least partially degassed fluid through the inner lumen, a pump can be activated to deliver fluid through a mass exchanger. The mass exchanger can at least partially degas the fluid, and the at least partially degassed fluid can flow from the mass exchanger and into the inner lumen of the elongate body. Delivering the at least partially degassed fluid through an inner lumen can include injecting the at least partially degassed fluid into a control unit and activating a pump to cause the pump to force the at least partially degassed fluid through the inner lumen. The fluid can include saline. Further, in some embodiments, prior to delivering at least partially degassed fluid through the inner lumen of the elongate body, a sensor can be operated to determine an amount of a gas in the at least partially degassed fluid.

In another aspect, a method for ablating tissue is provided that includes contacting a tissue mass with an ablation element having at least one outlet port formed thereon, and delivering fluid through the at least one outlet port, where the fluid is at least partially degassed such that the fluid contains one or more gases having a predetermined pressure and mixture. The method further includes delivering energy to the ablation element to ablate the tissue mass.

BRIEF DESCRIPTION OF DRAWINGS

This invention will be more fully understood from the following detailed description taken in conjunction with the accompanying drawings, in which.

DETAILED DESCRIPTION

Figure 1:
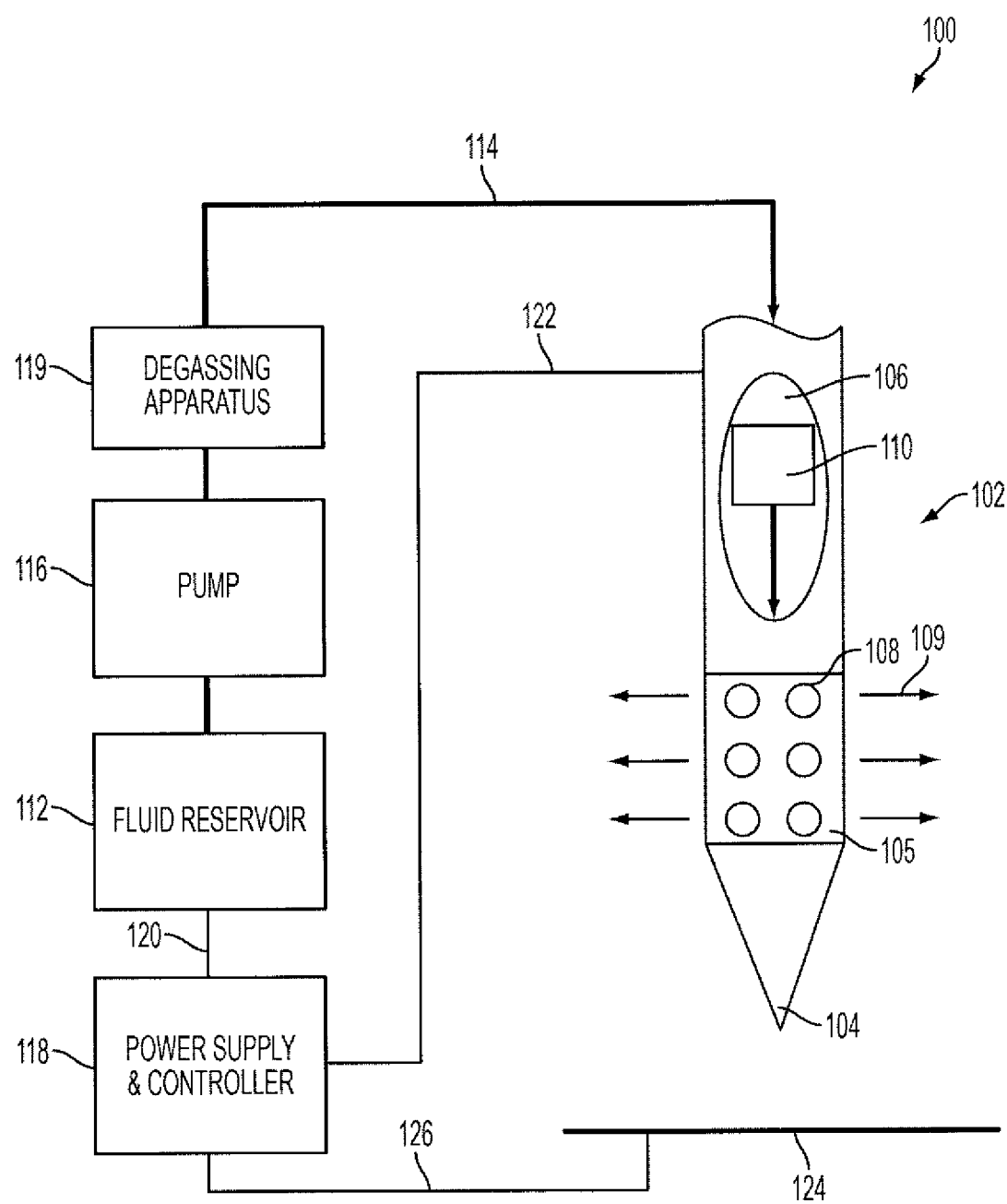
FIG. 1 is a diagram of one embodiment of a fluid enhanced ablation system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. Further, to the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape.

All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to use of "saline" as opposed to another fluid unless explicitly indicated. Other fluids can typically be used in a similar manner. Still further, to the extent the term "degas" or "degassing" is used herein, such term is meant to include any amount of degassing, including the removal of a small amount of one or more gases from the fluid or the removal of all of one or more gases from the fluid.

Fluid Enhanced Ablation Systems

The present invention is generally directed to degassed fluids used in conjunction with fluid enhanced ablation devices and treatments. Fluid enhanced ablation, as mentioned above, is defined by passing a fluid into tissue while delivering therapeutic energy from an ablation element. The delivery of therapeutic energy into tissue can cause hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

Fluid enhanced ablation, such as the SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. Delivering heated fluid enhances the ablation treatment because the fluid flow through the extracellular space of the treatment tissue can increase the heat transfer through the tissue by more than a factor of twenty. The flowing heated fluid therefore convects thermal energy from the ablation energy source further into the target tissue. In addition, the fact that the fluid is heated to a therapeutic temperature increases the amount of energy that can be imparted into the tissue. The fluid can also be at least partially degassed, which can further enhance the effectiveness of the fluid application as described below. Finally, the fluid can also serve to constantly hydrate the tissue and prevent any charring and associated impedance rise.

Figure 2:
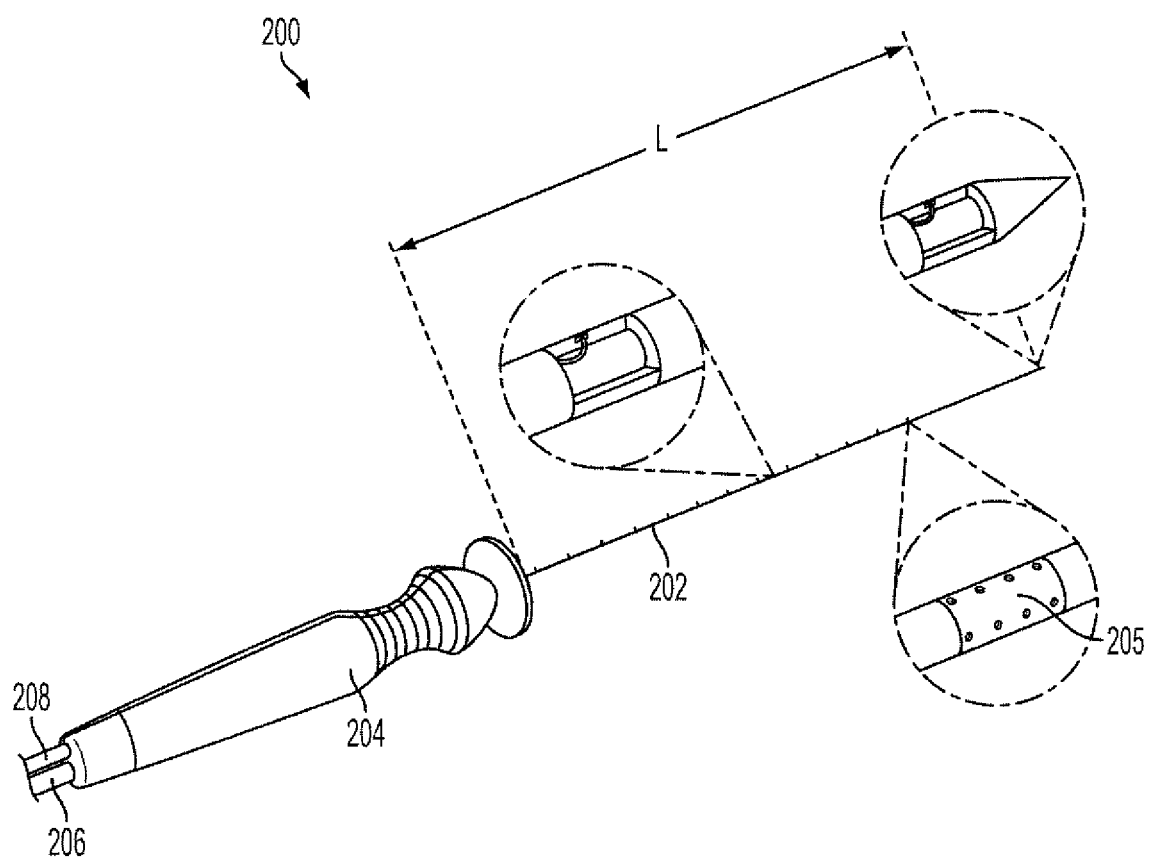
FIG. 2 is a perspective view of one embodiment of a medical device having an elongate body for use in fluid enhanced ablation.

FIG. 1 illustrates a diagram of one exemplary fluid ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 millimeters to about 1.65 millimeters), and having a length L (e.g., as shown in FIG. 2) that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated in 1.5 mil of the fluoropolymer Xylan™ 8840. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body.

In other embodiments, the electrode can be formed from a variety of other materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 105 or other ablation element can include one or more outlet ports 108 that are configured to deliver fluid from an inner lumen 106 extending through the elongate body 102 into surrounding tissue (as shown by arrows 109). Alternatively, the electrode 105 can be positioned near one or more outlet ports 108 formed in the elongate body 102. In many embodiments, it can be desirable to position the electrode adjacent to the one or more outlet ports to maximize the effect of the flowing fluid on the therapy. The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109 in FIG. 1, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. By way of example, in one embodiment, twenty-four equally-spaced outlet ports 108 having a diameter of about 0.4 mm can be created around the circumference of the electrode 105 using Electrical Discharge Machining (EDM). One skilled in the art will appreciate that additional manufacturing methods are available to create the outlet ports 108. In addition, in some embodiments, the outlet ports can be disposed along a portion of the elongate body adjacent to the electrode, rather than being disposed in the electrode itself.

The inner lumen 106 that communicates with the outlet ports 108 can also house a heating assembly 110 configured to heat fluid as it passes through the inner lumen 106 just prior to being introduced into tissue. Furthermore, the portion of the elongate body located distal to the electrode 105 or other ablation element can be solid or filled such that the inner lumen 106 terminates at the distal end of the electrode 105. In one embodiment, the inner volume of the portion of the elongate body distal to the electrode is filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Fluid can be supplied to the inner lumen 106 and heating assembly 110 from a fluid reservoir 112. The fluid can be at least partially degassed, as described in more detail below. In some embodiments, the fluid can be degassed prior to introduction into the reservoir of the system, while in some embodiments, such as the embodiment shown in FIG. 1, an apparatus 119 for degassing fluid can be incorporated into the system, as also described further below. The fluid reservoir 112, and the degassing apparatus 119 if provided, can be connected to the inner lumen 106 via a fluid conduit 114. The fluid conduit 114 can be, for example, flexible plastic tubing. The fluid conduit 114 can also be a rigid tube, or a combination of rigid and flexible tubing.

Fluid can be urged from the fluid reservoir 112, into the degassing apparatus 119 if provided, and into the inner lumen 106 by a pump 116. The pump 116 can be a syringe-type pump that produces a fixed volume flow with advancement of a plunger (not shown). An example of such a pump is a Model 74900 sold by Cole-Palmer Corporation of Chicago, IL. Other types of pumps, such as a diaphragm pump, may also be employed.

The pump 116, and/or degassing apparatus 119 if provided, can be controlled by a power supply and controller 118. The power supply and controller 118 can deliver electrical control signals to the pump 116, and/or degassing apparatus 119 if provided, to cause the pump to produce a desired flow rate of fluid. The power supply and controller 118 can be connected to the pump 116 via an electrical connection 120. The power supply and controller 118 can also be electrically connected to the elongate body 102 via connection 122, and to a collector electrode 124 via connection 126. In addition, the power supply and controller 118 can be connected to one or more of the heating assembly 110, the degassing apparatus 119 if provided, and/or a sensor (not shown) for determining one or more parameters of the fluid, such as an amount or a percentage of gas in the fluid, if provided, through similar electrical connections (not shown). The pump 116, power source and controller 118, degassing apparatus 119, and other components can generally be considered as part of a control unit for at least partially degassing and pumping fluid to a treatment site.

The collector electrode 124 can have a variety of forms. For example, the collector electrode 124 can be a large electrode located outside a patient's body. In other embodiments, the collector electrode 124 can be a return electrode located elsewhere along the elongate body 102, or it can be located on a second elongate body introduced into a patient's body near the treatment site.

In operation, the power supply and controller 118 can drive the delivery of fluid through a degassing apparatus, if provided, and into target tissue at a desired flow rate, the heating of the fluid to a desired therapeutic temperature, and the delivery of therapeutic ablative energy via the one or more ablation elements, such as electrode 105. To do so, the power supply and controller 118 can itself comprise a number of components for generating, regulating, and delivering required electrical control and therapeutic energy signals. For example, the power supply and controller 118 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 122 and the elongate body 102 such that RF energy is passed between the emitter electrode 105 and the collector electrode 124 that can be located remotely on a patient's body. In embodiments in which the elongate body is formed from non-conductive material, the one or more electrical connections 122 can extend through the inner lumen of the elongate body or along its outer surface to deliver current to the emitter electrode 105. The passage of RF energy between the ablation element and the collector electrode 124 can heat the tissue surrounding the elongate body 102 due to the inherent electrical resistivity of the tissue. The power supply and controller 118 can also include a directional coupler to feed a portion of the one or more RF signals to, for example, a power monitor to permit adjustment of the RF signal power to a desired treatment level.

The elongate body 102 illustrated in FIG. 1 can be configured for insertion into a patient's body in a variety of manners. FIG. 2 illustrates one embodiment of a medical device 200 having an elongate body 202 disposed on a distal end thereof configured for laparoscopic or direct insertion into a target area of tissue. In addition to the elongate body 202, the device 200 can include a handle 204 to allow an operator to manipulate the device. The handle 204 can include one or more electrical connections 206 that connect various components of the elongate body (e.g., the heating assembly and ablation element 205) to, for example, the power supply and controller 118 and the degassing apparatus 119, if provided, described above. The handle 204 can also include at least one fluid conduit 208 for connecting a fluid source to the device 200.

While device 200 is one exemplary embodiment of a medical device that can be adapted for use in fluid enhanced ablation, a number of other devices can also be employed. For example, a very small elongate body can be required in treating cardiac dysrhythmias, such as ventricular tachycardia. In such a case, an appropriately sized elongate body can be, for example, disposed at a distal end of a catheter configured for insertion into the heart via the circulatory system. In one embodiment, a stainless steel needle body between about 20- and about 25-gauge (i.e., an outer diameter of about 0.5 millimeters to about 0.9 millimeters) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters).

Therapeutic Treatment Using Fluid Enhanced Ablation

Ablation generally involves the application of high or low temperatures to cause the selective necrosis and/or removal of tissue. There is a known time-temperature relationship in the thermal destruction of tissue accomplished by ablation. A threshold temperature for causing irreversible thermal damage to tissue is generally accepted to be about 41° Celsius (C). It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as:

$$t_{eq.43°\,C.} = \int R^{(T(t)-43°)} dt \quad (1)$$

where T is the tissue temperature and R is a unit-less indicator of therapeutic efficiency in a range between 0 and 5 (typically 2 for temperatures greater than or equal to 43° C., zero for temperatures below 41° C., and 4 for temperatures between 41 and 43° C.), as described in Sapareto S. A. and W. C. Dewey, *Int. J. Rad. Onc. Biol. Phys.* 10(6):787-800 (1984). This equation and parameter set represents just one example of the many known methods for computing a thermal dose, and any of methodology can be employed with the methods and devices of the present invention. Using equation (1) above, thermal doses in the range of $t_{eq,43°\,C.}$=20 minutes to 1 hour are generally accepted as therapeutic although there is some thought that the dose required to kill tissue is dependent on the type of tissue. Thus, therapeutic temperature may refer to any temperature in excess of 41° C., but the delivered dose and, ultimately, the therapeutic effect are determined by the temporal history of temperature (i.e., the amount of heating the tissue has previously endured), the type of tissue being heated, and equation (1). For example, Nath, S. and Haines, D. E., *Prog. Card. Dis.* 37(4):185-205 (1995) (Nath et al.) suggest a temperature of 50° C. for one minute as therapeutic, which is an equivalent time at 43° C. of 128 minutes with R=2. In addition, for maximum efficiency, the therapeutic temperature should be uniform throughout the tissue being treated so that the thermal dose is uniformly delivered.

Figure 3:
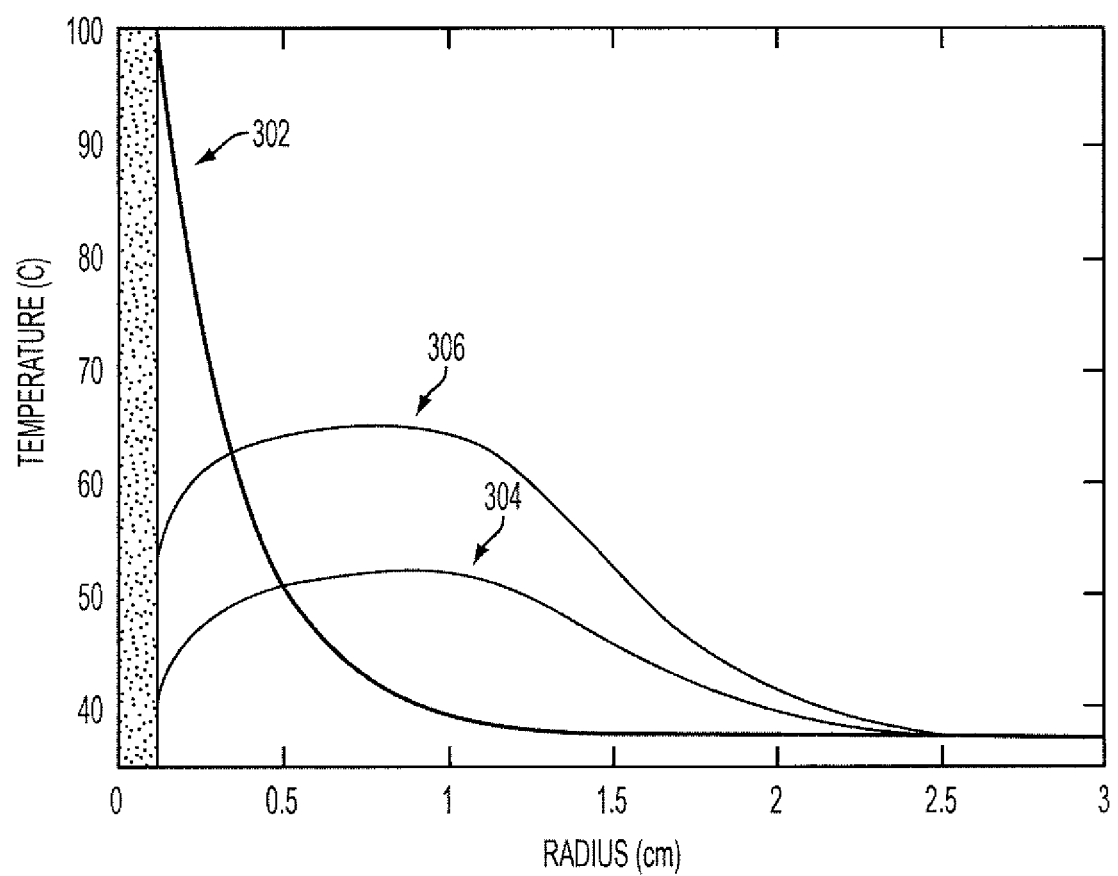
FIG. 3 is a graphical representation of simulated heating profiles for various forms of ablation.

FIG. 3 illustrates the performance profiles of several ablation techniques by showing a simulated temperature achieved at a given distance from an ablation element, such as electrode 105. The first profile 302 illustrates the performance of RF ablation without the use of fluid enhancement. As shown in the figure, the temperature of the tissue falls very sharply with distance from the electrode. This means that within 10 millimeters of the ablation element the temperature of the tissue is still approximately body temperature (37° C.), far below the therapeutic temperature of 50° C. discussed above. Furthermore, very close to the ablation element the temperature is very high, meaning that the tissue will more quickly desiccate, or dry up, and char. Once this happens, the impedance of the tissue rises dramatically, making it difficult to pass energy to tissue farther away from the ablation element.

A second tissue temperature profile 304 is associated with a second prior art system similar to that described in U.S. Pat. No. 5,431,649. In this second system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 304 is more uniform than profile 302, but the maximum temperature achieved anywhere is approximately 50° C. Thus, the temperature profile 304 exceeds the generally accepted tissue damaging temperature threshold specified for one minute of therapy in only a small portion of the tissue. As described above, such a small temperature increment requires significant treatment time to achieve any therapeutically meaningful results.

A third tissue temperature profile 306 is achieved using the teachings of the present invention. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 306 is both uniform and significantly above the 50° C. therapeutic threshold out to 15 millimeters from the electrode. Moreover, because the temperature is uniform within this volume, the thermal dose delivered is also uniform through this volume.

The uniform temperature profile seen in FIG. 3 can be achieved by the introduction of heated fluid into the target tissue during application of ablative energy. The fluid convects the heat deeper into the tissue, thereby reducing the charring and impedance change in tissue that occurs near the ablation element, as shown in profile 302. Further, because the fluid is heated to a therapeutic level, it does not act as a heat sink that draws down the temperature of the surrounding tissue, as seen in profile 304. Therefore, the concurrent application of RF energy and perfusion of heated saline solution into the tissue eliminates the desiccation and/or vaporization of tissue adjacent to the electrode, maintains the effective tissue impedance, and increases the thermal transport within the tissue being heated with RF energy. The total volume of tissue that can be heated to therapeutic temperatures, e.g., greater than 41° C., is thereby increased. For example, experimental testing has demonstrated that a volume of tissue having a diameter of approximately 8 centimeters (i.e., a spherical volume of approximately 156 $cm^3$) can be treated in 5 minutes using the fluid enhanced ablation techniques described herein. By comparison, conventional RF can only treat volumes having a diameter of approximately 3 centimeters (i.e., a spherical volume of approximately 14 cm$^3$) in the same 5-minute time span.

In addition, fluid enhanced ablation devices according to the present invention have a greater number of parameters that can be varied to adjust the shape of the treatment profile according to the tissue being treated. For example, when using the SERF ablation technique, an operator or control system can modify parameters such as saline temperature (e.g., from about 40° C. to about 80° C.), saline flow rate (e.g., from about 0 ml/min to about 20 ml/min), the amount of degassing of the saline, RF signal power (e.g., from about 0 W to about 100 W), and duration of treatment (e.g., from about 0 minutes to about 10 minutes) to adjust the temperature profile 306 and improve the reproducibility of the therapy. In addition, different electrode configurations can also be used to vary the treatment. For example, although the emitter electrode 105 illustrated in FIG. 1 is configured as a continuous cylindrical band adapted for a mono-polar current flow, the electrode can also be formed in other geometries, such as spherical or helical, that form a continuous surface area, or the electrode may have a plurality of discrete portions. The electrodes may also be configured for bipolar operation, in which one electrode (or a portion of an electrode) acts as a cathode and another electrode (or portion thereof) acts as an anode.

A preferred fluid for use in the SERF ablation technique is sterile normal saline solution (defined as a salt-containing solution). However, other liquids may be used, including Ringer's solution, or concentrated saline solution. A fluid can be selected to provide the desired therapeutic and physical properties when applied to the target tissue and a sterile fluid is recommended to guard against infection of the tissue. The fluid can be further enhanced by at least partially removing a one or more dissolved gases from the fluid, such that the fluid contains one or more gases having a predetermined pressure and mixture. In some embodiments, this predetermined pressure and mixture can be less than a predetermined value for one or more of the gases. The remaining portions of the description are directed primarily to devices and methods for degassing fluid used in conjunction with fluid enhanced ablation therapy.

Fluid Degassing

Fluids commonly include one or more dissolved gases that can, under certain conditions, come out of solution in the form of gas bubbles. Exemplary gases commonly dissolved in fluid include oxygen, nitrogen, carbon dioxide, and other gases present in the atmosphere. Dissolved gases come out of solution according to the ability of a fluid to hold a particular gas in solution at a given temperature and pressure. This relationship is governed by Henry's Law, which states that at a particular temperature, the amount of a particular gas that dissolves in a particular type and volume of liquid is proportional to the partial pressure of the gas in equilibrium with the liquid. In other words, the amount of a gas that can be dissolved in a fluid depends on the temperature of the fluid, the pressure of the gas in the environment surrounding the fluid, as well as the type and volume of the fluid. For example, water and saline are commonly able to hold less gas in solution as the temperature of the fluid is increased. The increased kinetic energy of the gas molecules in the solution causes them to more easily escape the solution, resulting in lowered solubility.

In fluid enhanced ablation, fluid is heated just prior to introduction into tissue. The heating process reduces the solubility of the dissolved gases, resulting in one or more gases coming out of solution in the form of gas bubbles. These bubbles can form, for example, inside the inner lumen and can subsequently exit the outlet ports 108 into the tissue surrounding the elongate body 102. Furthermore, gas bubbles may also form just outside the elongate body due to heating from the emitter electrode 105. Gases that come out of solution during ablation therapy can have a detrimental effect on the control, and therefore the effectiveness, of the fluid supplied to the treatment site. This is primarily because the gas bubbles formed in the fluid are compressible, while the fluid itself is not. This compressibility, or compliance, is undesirable in a fluid enhanced ablation system. For example, a pump can be designed to advance a plunger on a fluid-filled syringe at a particular speed so as to induce a particular flow rate. As long as the fluid path contains only incompressible fluid, the flow rate can be maintained as a constant despite changes in back-pressure that can be caused by physiologic changes in the tissue, or by changes in fluid resistivity due to ablation therapy. However, if the fluid contains compressible gas bubbles, an increase in back-pressure from the tissue may alter the flow rate because the changing pressure can, at least in part, be absorbed by the compressible gas bubbles. Accordingly, any possible compliance of the fluid used in fluid enhanced ablation therapy should be reduced. This can be accomplished, for example, by removing at least some of the dissolved gas in the fluid. Removing dissolved gas from the fluid can increase the temperature at which gas comes out of solution, thereby reducing the compliance of a fluid enhanced ablation system in which the fluid is used. Using degassed fluids can increase the effectiveness, reproducibility, and overall reliability of fluid enhanced ablation systems.

Gas can be removed from the fluid in a variety of ways, some of which are described in greater detail below. These methods include degassing using one or more chemicals, boiling the fluid, exposing the fluid to a vacuum, and exposing the fluid to a gas having a desired gas concentration. While methods to remove gas from the fluid can be applied to remove substantially all of the gas within the fluid, in some embodiments it can be desirable to maintain some of the gas in the fluid. For example, in some instances it may be desirable to maintain some level of oxygen in the fluid or some level of carbon dioxide in the fluid. By way of non-limiting example, in one embodiment, it can be desirable to degas a fluid to a partial pressure of oxygen ($O_2$) in a range of about 20 mm to about 40 mm of mercury. These levels of oxygen can prevent the complete oxygen deprivation of tissues being treated with fluid enhanced ablation. Accordingly, the devices and methods of the present invention can be utilized to at least partially degas a fluid such that the fluid contains a predetermined concentration of a particular gas. In some embodiments, this can be accomplished by degassing a fluid such that the fluid contains less than a predetermined partial pressure of a particular gas. The predetermined partial pressure can be set as desired by a user.

Chemical degassing can be performed by adding one or more chemicals to the fluid that bind or otherwise react with dissolved gases within the fluid. The chemicals can be formulated or configured to remove one or more gases from the fluid. A person skilled in the art will recognize various chemicals or groups of chemicals that can target and remove one or more gases from the fluid. For example, oxygen can be selectively removed from a fluid by introducing a reductant, such as ammonium sulfite, into the fluid.

Degassing a fluid by boiling can be performed by heating the fluid for a period of time up to or above a temperature that can cause one or more gases to be removed. As the fluid heats up, its ability to hold gas in solution will decrease, and the gases within the fluid can begin to come out of solution and dissipate from the system. By way of example only, a volume of degassed saline having a desired salinity can be created by starting with diluted saline (e.g., saline diluted with water) and boiling the diluted saline until the remaining liquid has a desired salinity.

Boiling a fluid can be effective to remove a portion of all gasses within the fluid. Specific gases, however, can be more difficult to target using this method because the application of heat to the fluid can act on all gases within the fluid. However, different gasses can dissipate at different rates at the same temperature. Thus, selectively controlling the heating of a fluid can be effective to at least partially target the removal of a particular gas from the fluid. The fluid can be heated or boiled for any amount of time, depending at least in part on the desired percent gas concentration and the temperature to which the fluid is heated, however, in some embodiments the fluid can be heated to its boiling point for about 30 minutes.

An additional method for degassing a fluid includes exposing the fluid to a vacuum source, i.e., applying a vacuum to the fluid. Similar to boiling, applying a vacuum to a fluid can be effective to remove a portion of all gases within the fluid. While exemplary apparatuses for applying a vacuum to fluid are described in greater detail below, including apparatuses such as mass exchangers, a vacuum source can generally draw gas from the fluid by reducing the atmospheric pressure surrounding the fluid, thereby drawing gas out of solution by equilibration forces. For instance, the fluid can be in a chamber and a vacuum source can be coupled to the chamber so that the vacuum source can apply a vacuum to the fluid within the chamber. The fluid can be exposed to a vacuum for any amount of time, depending at least in part on the desired percent gas concentration and a strength of the vacuum force applied to the fluid, however, in some embodiments the fluid can be exposed to a vacuum for at least about eight hours. This process can be accelerated by agitating the liquid while exposed to the vacuum to cause cavitation or to increase the surface area of the liquid contacting the vacuum.

Yet a further method for degassing a fluid includes exposing the fluid to one or more gas sources that contain a gas having a desired gas concentration, i.e., applying one or more gasses to the fluid. This is a variation on the vacuum concept, in which a vacuum (or "negative") gas source is employed to draw gas out of solution. By exposing a fluid to a particular concentration of gas for a period of time, the concentration of gas in the fluid can begin to equilibrate with the gas source so that the percentage of gas in the fluid approaches, and can eventually equal, the percentage of gas present in the gas source. Some exemplary apparatuses for applying a gas to a fluid are described in greater detail below, including mass exchangers. In some embodiments, the fluid can be in a chamber and a gas source can be coupled to the chamber so that the gas source can be in fluid communication with the chamber. When the fluid is within a chamber and gas is applied thereto, the chamber can be vented to allow excess gas that comes out of solution to escape. Further, the fluid and/or the gas being applied to the fluid can be agitated to speed up the equilibration process. A person skilled in the art will recognize a number of different ways by which agitation can be imparted on the system, for example, by applying a rotational force to either or both of the fluid chamber and the gas chamber.

A gas source applied to a fluid can contain a given concentration of a single gas, or a combination of a plurality of gases at particular partial pressures. Multiple gases can be applied to the fluid at the same time or in succession to achieve a desired concentration of one or more gases within the fluid. The fluid can be exposed to one or more of the gas sources for any amount of time, depending at least in part on the desired gas concentrations within the fluid and the gas concentrations of the applied gas. For example, in some embodiments the fluid can be exposed to a gas including a partial pressure of oxygen between about 20 mm and about 40 mm of mercury. As described above, exposing the fluid to such a gas can result in the fluid equilibrating until the fluid contains a partial pressure of oxygen that is also between about 20 mm and about 40 mm of mercury. Other gas sources can be utilized as well, or a single gas source having a predetermined concentration and mixture of a plurality of gases can be utilized. For example, in some embodiments it can be desirable to utilize a gas source that includes not only oxygen, but also carbon dioxide, as it can aid in maintaining the pH of the fluid. In such an embodiment, a gas source that includes a partial pressure of carbon dioxide between about 35 and about 40 mm of mercury can be utilized as a gas source.

Degassing in the Ablation Process

Fluid degassing can be performed at a number of different times in conjunction with fluid enhanced ablation therapy. In some embodiments, the fluid can be degassed prior to delivering the fluid into a reservoir. In such embodiments, the fluid can be degassed and then inserted into the fluid reservoir. Fluid degassed prior to introduction into the fluid reservoir can be sealed in an airtight container to prevent gas from re-entering into solution. Alternatively, the fluid can be degassed while in the fluid reservoir. In some embodiments, a fluid reservoir containing fluid that is at least partially degassed can be provided in a sterile container and/or can be pre-packaged in sterile packaging. The container can then be coupled to a fluid enhanced ablation therapy system. For example, degassed fluid can be loaded in a syringe and pre-packaged for use with a fluid enhanced ablation therapy system. In such embodiments, a sensor can be provided to gauge the concentration of a gas in a fluid. Gauging the concentration of a gas in a sealed fluid reservoir can be desirable to ensure that a faulty seal has not allowed gas to re-enter into solution in the fluid. Exemplary sensors are discussed in more detail below.

Alternatively, an apparatus for degassing fluid as shown in FIG. 1 can be provided in conjunction with the fluid enhanced ablation therapy system. The fluid reservoir 112 can provide fluid to the degassing apparatus 119, the apparatus 119 can degas the fluid flowing therethrough using the methods described herein or other methods for degassing fluid, and then the fluid can flow through the conduit 114 and into the elongate body 102 for use in ablation. In still further alternative embodiments, the degassing apparatus 119 can be disposed upstream of the fluid reservoir 112 such that fluid is supplied from an initial source (not shown), passed through the degassing apparatus 119 for purposes of degassing the fluid, and the fluid can then be stored in the fluid reservoir 112 for use proximate to the treatment site as described above. Some exemplary embodiments of apparatuses for use in degassing fluid are described in greater detail below.

Effects of Saline Degassing

Figure 4:
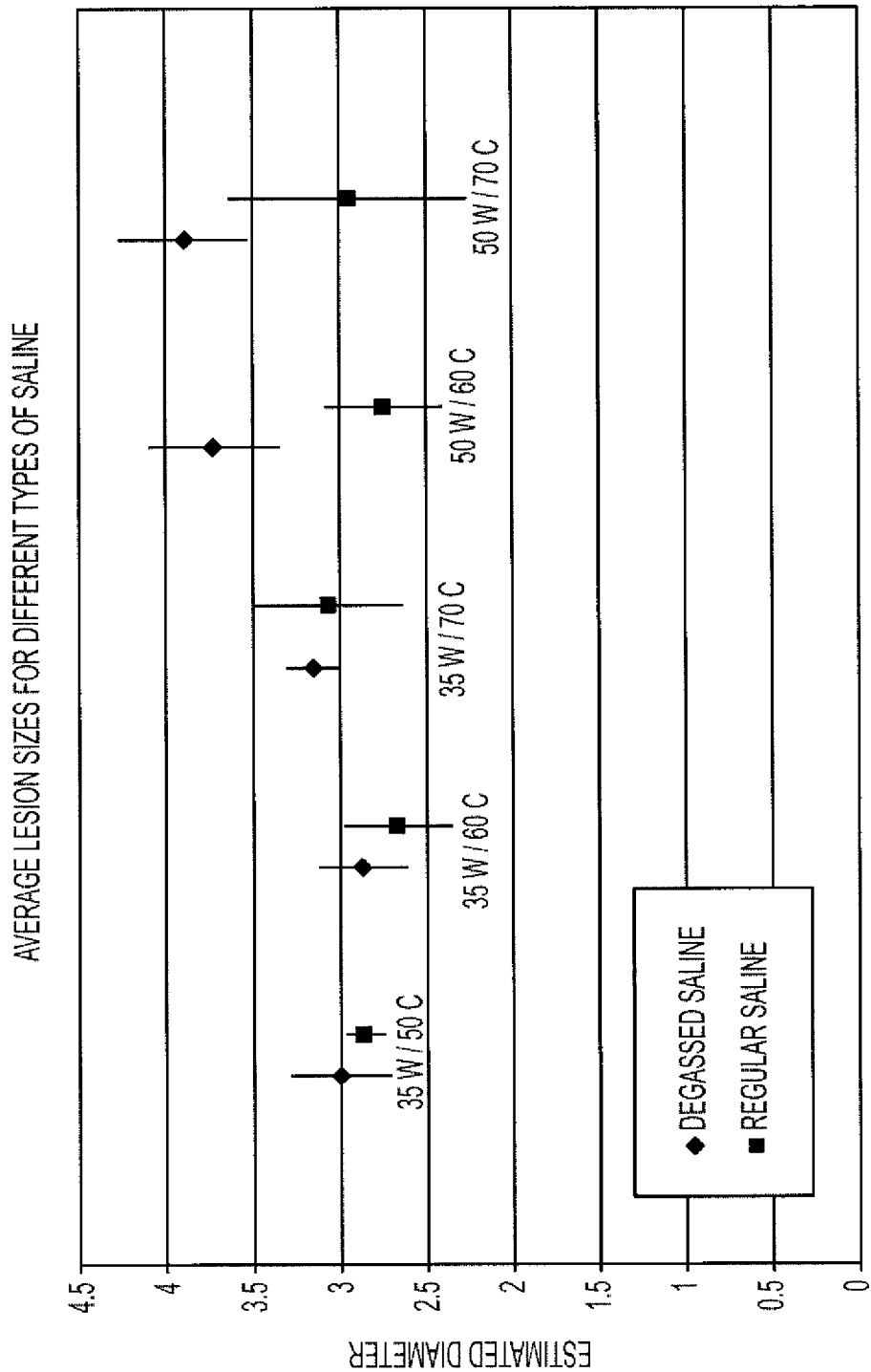
FIG. 4 is a graphical representation of performance profiles for various types of saline at different temperatures and supplied powers.

FIG. 4 illustrates the performance profiles of saline that was not degassed (labeled as "regular saline") and saline that was at least partially degassed. To produce the results shown in FIG. 4, degassed saline was obtained by boiling 600 ml of regular saline and 200 ml of pure water together for approximately 30 minutes. The boiling was allowed to continue until 600 ml of saline remained. The hot saline was then sealed in a flask and cooled. This created a partial vacuum, which helped to prevent atmospheric gas from dissolving back into the newly degassed saline. This procedure produced 600 ml of saline with measured dissolved oxygen levels of approximately 1 mg/L. The same saline, at equilibrium at room temperature and pressure, typically contains approximately 8 mg/L of dissolved oxygen.

The chart shows the approximate diameter of lesions created using saline with the two different concentrations of dissolved gas at different therapy settings of saline temperature and RF power level. The experiments for the two saline gas concentrations involved a 10 ml/min rate of flow and each experiment was replicated five times. The results illustrate the mean lesion diameter for various temperatures and power levels, and the standard deviation for the same. As shown, the degassed saline allows for lesions of larger diameters to be achieved across a range of temperature and power levels. As the amount of RF power increases and/or saline temperature increases—both conditions under which gas is more likely to come out of solution—the disparity increases between the lesion sizes created with degassed saline and those created with regular saline. The degassed saline shows an ability to consistently achieve larger and less variable lesion diameters. Accordingly, the use of at least partially degassed saline in fluid enhanced ablation therapy can contribute significantly to the reliability and effectiveness of the treatment, especially at higher power levels and temperatures.

Apparatuses for Degassing Fluid

Just as fluid can be degassed in a variety of manners, a number of different apparatuses can be used to degas fluid. Exemplary apparatuses can include a container or chamber in which the fluid is disposed and the degassing methods discussed above applied directly thereto (e.g., applying a chemical, vacuum, or gas to the chamber and/or heating the chamber as described above), or the apparatus can be more elaborate, such as a mass exchanger. An exemplary mass exchanger is the Cell-Pharm® Hollow-Fiber Oxygenator manufactured by CD Medical. One exemplary embodiment of an apparatus 310 for use in degassing fluid is illustrated in FIGS. 5-7.

Figure 5:
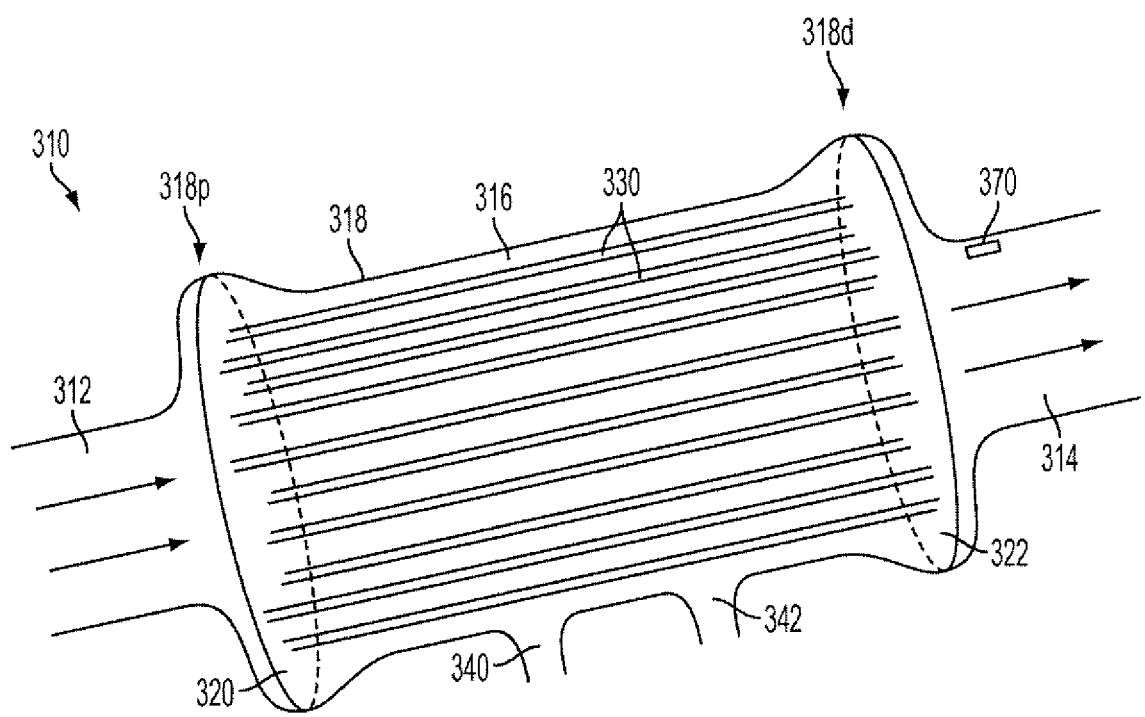
FIG. 5 is a perspective view of one exemplary embodiment of a mass exchanger for use in conjunction with a fluid enhanced ablation system.
Figure 6:
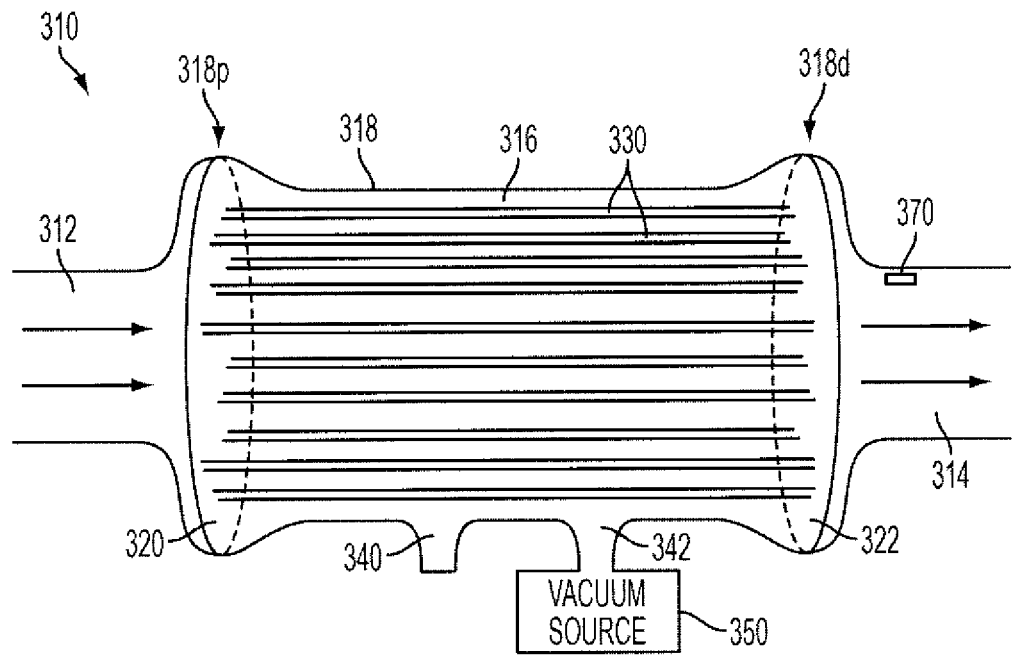
FIG. 6 is a side, semi-transparent view of the mass exchanger of FIG. 5 having a vacuum source coupled thereto.
Figure 7:
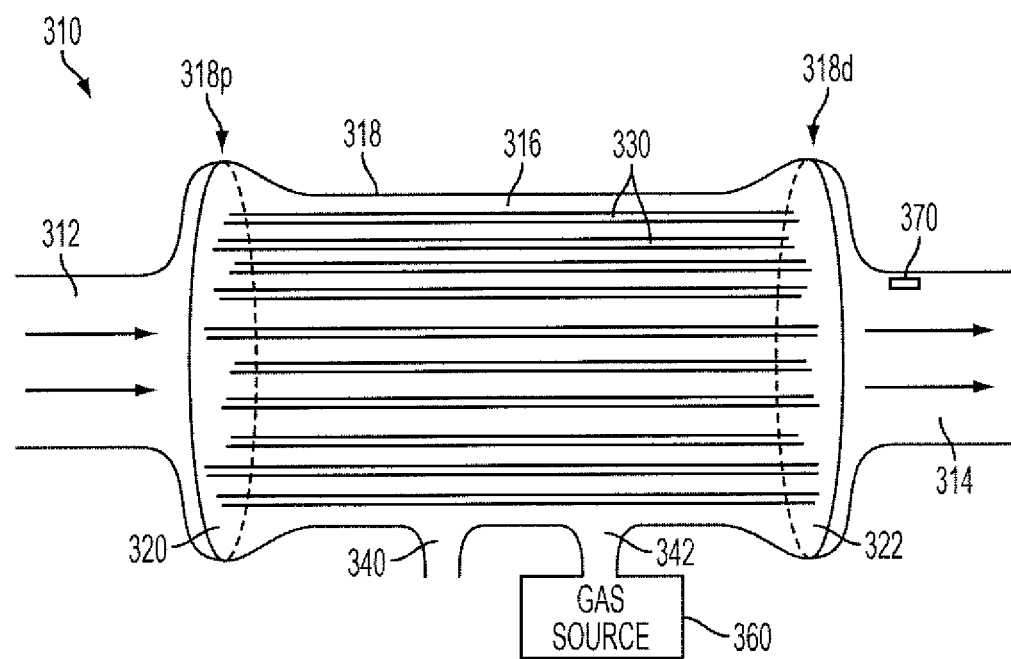
FIG. 7 is a side, semi-transparent view of the mass exchanger of FIG. 5 having a gas source coupled thereto.

The apparatus 310 shown in FIGS. 5-7 is a mass exchanger having a plurality of tubes 330 that are gas permeable and substantially fluid impermeable. The apparatus 310 can include an inlet 312 for receiving fluid to be treated (i.e., have at least a portion of gas removed therefrom), an outlet 314 for ejecting treated fluid, and a treatment chamber 316 disposed therebetween. The treatment chamber 316 can include one or more tubes 330 in fluid communication with the inlet 312 and the outlet 314 such that fluid can flow from the inlet 312, through the tubes 330, and out of the outlet 314. In the illustrated embodiment, the tubes 330 are disposed at each end in proximal and distal discs 320, 322. The proximal disc 320 can block fluid from flowing through the treatment chamber 316 such that fluid that enters through the inlet 312 can only pass through the chamber 316 via the tubes 330. Likewise, the distal disc 322 can prevent fluid that passes across the chamber 316 via the tubes 330 from back-flowing into the chamber 316.

One or more gas outlets or ports 340, 342 can be part of the chamber 316. The gas ports 340, 342 can allow various components, such as a vacuum source 350 (FIG. 6) or a gas source 360 (FIG. 7), to be connected to the treatment chamber 316 such that the components 350, 360 can be in fluid communication with the treatment chamber 316. The gas sources 350, 360 can then be operated as described herein to at least partially degas the fluid. The ports 340, 342 can be selectively opened and closed based on a desired treatment of the fluid flowing through the tubes 330. In some embodiments, a sensor 370 for determining at least one parameter of a fluid flowing through the apparatus 310 can be disposed at or proximate to the outlet 314. The sensor 370 can be configured to measure any number of parameters, but in some exemplary embodiments the sensor 370 can be configured to measure a concentration of gas in a fluid passing through the outlet 314.

A housing 318 of the apparatus 310, in which the treatment chamber 316 is disposed, can be sized and shaped in any number of ways so that fluid can flow therethrough while at least a portion of a gas dissolved within the fluid can be removed. As shown in the figure, the housing 318 is generally cylindrical and is sized to allow the plurality of tubes 330 to be spatially disposed therein. The housing 318 can be larger than the respective inlet 312 and outlet 314 disposed near the proximal and distal ends 318$p$, 318$d$ of the housing 318, as shown, or the housing can have the same or a smaller outer diameter than the inlet and/or outlet. The inlet 312 and the outlet 314 can likewise be sized and shaped in any number of ways, and as shown they are generally cylindrical and sized to allow fluid to flow therethrough. One skilled in the art will appreciate that the dimensions of any of these components can vary depending on the location of the apparatus in the fluid delivery system.

The one or more tubes 330 disposed in the treatment chamber 316 can be gas permeable and substantially fluid impermeable. Thus, fluid that enters the tubes 330 can generally flow through the tubes 330, while gases disposed in the fluid can dissipate out of the tubes 330 when particular environments are produced within the treatment chamber 316 (e.g., by the application of a vacuum or other gas source). Many different materials can be used to form gas permeable and substantially fluid impermeable walls, including, for example, microporous polyethylene fibers or expanded polytetrafluoroethylene (PTFE), such as is available from W.L. Gore & Associates, Inc. The tubes 330 can be sized and shaped in any number of ways, but as shown the tubes 330 are generally elongate, extend substantially across a length of the treatment chamber 316, and are substantially cylindrical in shape. Space can be provided between the tubes 330 so that gas removed from fluid flowing through the tubes 330 can dissipate into the treatment chamber 316 and possibly out of one of the gas ports 340, 342, discussed in more detail below. Any number of tubes 330 can be used, with the flow rate of the fluid being based, at least in part, on the number and diameter of the tubes 330.

The discs 320, 322 can be configured in a manner that allows the treatment chamber 316 to be separated from the inlet 312 and outlet 314. Thus, fluid entering the inlet 312 can generally only flow across the treatment chamber 316 by passing through the tubes 330 and cannot generally enter the chamber 316 through the inlet 312 or by back-flowing into the chamber 316 near the outlet 314. Accordingly, a diameter of the discs 320, 322 can be substantially equal to an inner diameter of the housing 318 at the proximal and distal ends 318p, 318$d$ of the housing 318. Further, a connection between the ends of the tubes 330 and the discs 320, 322 in which the tubes 330 can be disposed can generally be fluid-tight such that fluid cannot generally flow into the chamber 316 between the tubes 330 and the respective disc 320, 322. While a variety of materials can be used to form the discs 320, 322, in one exemplary embodiment an epoxy is used to form the discs 320, 322.

The gas ports 340, 342 can generally be configured to allow a vacuum or gas to be applied to the treatment chamber 316 between the proximal and distal discs 320, 322. Thus, the ports 340, 342 can be in fluid communication with the treatment chamber 316. In the embodiment shown in FIG. 5, the ports 340, 342 are open, but in one exemplary use, shown in FIG. 6, a vacuum source 350 can be coupled to one of the ports 342 and the other port 340 can be closed so that a vacuum can be created within the treatment chamber 316. Applying a vacuum to the treatment chamber 316 can draw gas from fluid passing through the tubes 330 through the gas-permeable walls of the tubes 330 and into the treatment chamber 316. As discussed above, the vacuum source 350 can be applied to create a desired percent concentration of gas in the fluid passing through the tubes 330.

In another exemplary use of the ports 340, 342, shown in FIG. 7, a gas source 360 can be coupled to one of the ports 342 and the other port 342 can remain open. The gas source 360 can have a desired concentration level of one or more particular gases. As the gas is supplied to the treatment chamber 316, the gas in the chamber 316 and the gas in the fluid can begin to equilibrate. Excess gas from the fluid can dissipate out of the fluid, through the gas-permeable walls of the tubes 330, and into the chamber 316. As the system continues to equilibrate, excess gas can flow out of the open gas port 342, thus creating a substantially uniform percent concentration of gas in the fluid flowing through the tubes 330 and the chamber 316. As described above, any number of gases can be supplied simultaneously or consecutively to achieve various percent concentrations of gas in the fluid.

The sensor 370 at the distal end of the apparatus 310 can be any number of sensors and it can be configured to measure any number of parameters of the system. In one exemplary embodiment, the sensor 370 can be configured to measure a percent concentration of gas in a fluid located proximate to the outlet 314. For example, the sensor 370 can be an oxygen sensor. While the sensor 370 is shown in the distal end 318d of the housing 318, in other embodiments one or more sensors 370 can be disposed in other locations of the apparatus 310, or in other portions of the system. By way of non-limiting example, a sensor for measuring parameters such as the percent concentration of gas in a fluid can be disposed in the elongate body 102, proximate to the treatment site (FIG. 1).

While sample shapes and sizes are provided herein for the various components of the apparatus 310, a person skilled in the art will recognize that the size and shape of the apparatus 310 and its components can depend on a number of factors, including, at least in part, the size and shape of the other components. For example, a size of the components of the degassing apparatus 310 that is used in conjunction with a fluid enhanced ablation therapy system can be sized relative to the other fluid enhanced ablation therapy system components, while a size of the components of the degassing apparatus 310 that is used to degas the fluid prior to associating a fluid reservoir with the fluid enhanced ablation therapy system can be larger because its size does not need to generally account for the size of other components of the fluid enhanced ablation therapy system.

Integration Into Ablation Systems

In embodiments in which the fluid is degassed separately from the fluid enhanced ablation system, the system can operate in a manner as described with respect to FIG. 1 but with the degassing apparatus 119 being separate from the system. The fluid can be degassed in any number of manners as described herein or otherwise known in the art, and then it can be coupled to or delivered into the fluid enhanced ablation system for application proximate to the treatment site. In embodiments in which the fluid is degassed as part of the fluid enhanced ablation therapy system, the system can operate in a manner similar as described with respect to FIG. 1. The degassing apparatus 310, or equivalents thereof, can be supplied as the degassing apparatus 119 of FIG. 1. Accordingly, fluid can be pumped from the fluid reservoir 112 by the pump 116 into the inlet 312 of the degassing apparatus 310. The fluid can then pass across the treatment chamber 316 via the tubes 330 and into the outlet 314. As the fluid flows through the tubes 330, degassing forces, such as a force supplied by a vacuum source and/or another gas source, can be applied to the fluid so that gas can be selectively removed from the fluid in the tubes 330. Fluid from the outlet can then continue to be pumped by the pump 116 into the conduit 114 for application proximate to the treatment site.

Methods of Use

As described above, the various embodiments of the devices and systems disclosed herein can be utilized in a variety of surgical procedures to treat a number of medical conditions. For example, medical devices as disclosed herein can be configured for insertion into a target volume of tissue directly during an open surgical procedure or during percutaneous ablation therapy. Alternatively, the medical devices can be configured to be passed through one or more layers of tissue during a laparoscopic or other minimally invasive procedure. Furthermore, the devices can be configured for introduction into a patient via an access port or other opening formed through one or more layers of tissue, or via a natural orifice (i.e., endoscopically). Depending on the device employed, delivery may be facilitated by directly inserting the elongate body as shown in FIG. 2, or by introducing a catheter containing an elongate body through, for example, a patient's circulatory system. Following delivery to a treatment site, a portion of a surgical device, e.g., a distal portion of the elongate body 102, can be inserted into a target treatment volume such that an ablation element is disposed within the treatment volume. In some embodiments, the ablation element can be positioned near the center of the treatment volume.

Once the device is positioned within the treatment volume, fluid can be delivered through the device into the treatment volume. The heating assemblies disclosed herein can be utilized to deliver fluid, such as the at least partially degassed fluid disclosed herein, at a therapeutic temperature, as described above. Alternatively, in some embodiments, the fluid can be delivered without first being heated to a therapeutic temperature. The fluid introduced into the target volume of tissue can be degassed on demand (e.g., as it flows from a reservoir to the treatment volume) by, for example, a degassing apparatus as described above, or can be degassed prior to storage in the fluid reservoir. Furthermore, the amount of degassing can be tested using, for example, a sensor either prior to or during ablation therapy. In addition to delivering fluid to the treatment volume, one or more ablation elements can be activated to simultaneously deliver therapeutic energy, such as RF energy, into the tissue in the treatment volume. In some embodiments, however, the one or more ablation elements need not be activated, and therapy can be administered by delivering therapeutically heated fluid from the elongate body alone. After a period of time, or depending on one or more feedback indications (e.g., a reading from a temperature sensor disposed within the treatment volume), the ablation element can be deactivated and the flow of fluid into the volume can be stopped. The device can then be removed and/or repositioned if additional therapy is required.

In other embodiments, degassed fluid can also be utilized with other types of ablation procedures. For example, unheated degassed fluid can be introduced through a conventional shower-head ablation electrode that is configured to contact, but not penetrate, a treatment volume. The use of a degassed fluid can still be advantageous when utilizing unheated fluid because the fluid can still experience heating in the vicinity of the ablation element.

Sterilization and Reuse

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the surgical devices disclosed herein may be disassembled partially or completely. In particular, the elongate body 202 of the medical device 200 shown in FIG. 2 may be removed from the handle 204, or the entire handle and elongate body assembly may be decoupled from the electrical and fluid connections 206, 208. In yet another embodiment, the handle, elongate body, and connections may be removably coupled to a housing that contains, for example, the fluid reservoir, degassing apparatus, pump, and power supply and controller shown in FIG. 1.

Further, the degassing apparatuses described herein may also be disassembled partially or completely. In particular, a degassing apparatus similar to the apparatus 310 can be disconnected from a fluid enhanced ablation system and cleaned or otherwise sterilized by, for example, passing a cleaning fluid through the apparatus. Still further, in some embodiments, the apparatus can be configured to disassemble such that individual components, such as each tube 330, can be removed and cleaned individually, or replaced.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An ablation system, comprising:
   an elongate body having an inner lumen configured to deliver fluid into a tissue mass adjacent to the elongate body;
   an ablation element configured to heat the tissue mass adjacent to the elongate body; and
   a fluid source separate from the elongate body and in fluid communication with the inner lumen for delivering fluid through the inner lumen, the fluid source containing a volume of fluid that is at least partially degassed such that the fluid contains one or more dissolved gases having less than a predetermined partial pressure.

2. The system of claim 1, further comprising a pump coupled to the fluid source and configured to pump fluid from the fluid source through the inner lumen of the elongate body.

3. The system of claim 1, further comprising a mass exchanger coupled to the fluid source and configured to at least partially degas the fluid.

4. The system of claim 1, wherein the fluid source comprises a syringe configured to couple to the elongate body for delivering fluid to the inner lumen.

5. The system of claim 1, wherein the fluid comprises saline.

6. The system of claim 1, further comprising a sensor configured to measure an amount of the gas in the fluid.

7. The system of claim 1, further comprising a heating assembly disposed within the inner lumen of the elongate body and configured to heat the fluid to be delivered from the elongate body.

8. The system of claim 1, wherein a partial pressure of oxygen contained in the fluid is in a range of about 20 mm to about 40 mm of mercury.

9. The system of claim 8, wherein the fluid comprises saline.

10. The system of claim 8, wherein at least a distal portion of the elongate body is configured to be inserted into the tissue mass.

11. The system of claim 8, further comprising a heating assembly disposed within the inner lumen of the elongate body and configured to heat the fluid to be delivered from the elongate body.

12. The system of claim 8, wherein the fluid source comprises a syringe configured to couple to the elongate body for delivering fluid to the inner lumen.

13. The system of claim 8, further comprising a mass exchanger coupled to the fluid source and configured to at least partially degas the fluid.

14. The system of claim 1, wherein at least a distal portion of the elongate body is configured to be inserted into the tissue mass.

15. The system of claim 1, wherein the elongate body includes a tissue-puncturing distal tip.

16. The system of claim 15, wherein the tissue-puncturing distal tip is a pointed tip.

17. The system of claim 1, wherein the fluid consists essentially of normal saline solution.

18. The system of claim 1, wherein the fluid consists essentially of concentrated saline solution.

19. The system of claim 1, wherein the fluid consists essentially of Ringer's solution.

20. The system of claim 1, wherein the one or more dissolved gases having less than the predetermined partial pressure are present in the fluid in a lower quantity than an amount expected at an equilibrium condition.

21. The system of claim 1, wherein the predetermined partial pressure is set by a user.

22. The system of claim 1, wherein the volume of fluid is at least partially degassed by reducing the atmospheric pressure surrounding the fluid.

23. The system of claim 1, wherein the fluid source containing the volume of fluid is sealed in an airtight container.

\* \* \* \* \*